United States Patent [19]

Ulbrich

[11] Patent Number: 4,836,208
[45] Date of Patent: * Jun. 6, 1989

[54] ELECTRODE ASSEMBLY FOR SENSING HEART ACTIVITY

[75] Inventor: Paul Ulbrich, San Ramon, Calif.

[73] Assignee: American Home Products Corporation (Del.), New York, N.Y.

[ * ] Notice: The portion of the term of this patent subsequent to Sep. 8, 2004 has been disclaimed.

[21] Appl. No.: 85,571

[22] Filed: Aug. 14, 1987

Related U.S. Application Data

[63] Continuation of Ser. No. 892,600, Aug. 1, 1986, Pat. No. 4,686,996, Continuation-in-part of Ser. No. 812,967, Dec. 24, 1985, abandoned.

[51] Int. Cl.⁴ ............................................. A61B 5/04
[52] U.S. Cl. .................................................... 128/642
[58] Field of Search ...................... 128/642, 784–786, 128/419 P, 361, 788

[56] References Cited

U.S. PATENT DOCUMENTS

| | | | |
|---|---|---|---|
| 3,750,650 | 8/1973 | Ruttgers | 128/642 |
| 4,311,153 | 1/1982 | Smits | 128/785 |
| 4,321,931 | 3/1982 | Hon | 128/642 |
| 4,437,467 | 3/1984 | Helfer et al. | 128/642 |
| 4,501,276 | 2/1985 | Lombardi | 128/642 |
| 4,577,635 | 3/1986 | Meredith | 128/642 |

FOREIGN PATENT DOCUMENTS 2738479  3/1979  Fed. Rep. of Germany ...... 128/642

Primary Examiner—Lee S. Cohen
Attorney, Agent, or Firm—Ronald W. Alice

[57] ABSTRACT

An electrode assembly for sensing heart activity and especially heart activity from a fetal epidermis during the birth of a child. A fetal electrode introducer includes a rigid guide tube with an intermediate universal joint which allows the guide tube to be bent at the best angle to accommodate each patient. The intermediate joint allows a smooth transmission of the rotary motion manually applied at a distal handle to drive the electrode into the fetal epidermis.

A sliding sleeve covers the fetal electrode to provide a bearing for rotation, protects the electrode from contamination, and also serves as a resistance means to indicate to the user that the assembly has abutted against the fetal epidermis. Such resisting means includes either a detent or lockable system, or a breakable membrane.

9 Claims, 3 Drawing Sheets

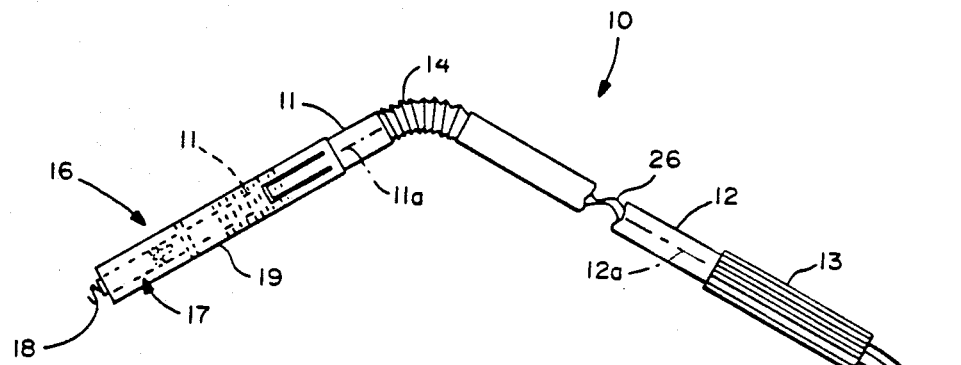
FIG.—1
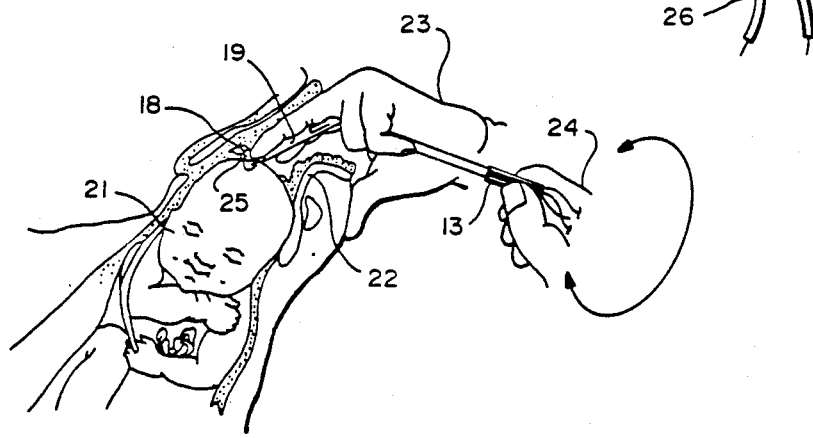
FIG.—2
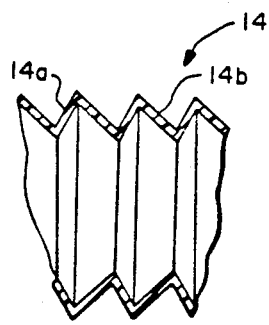
FIG.—3

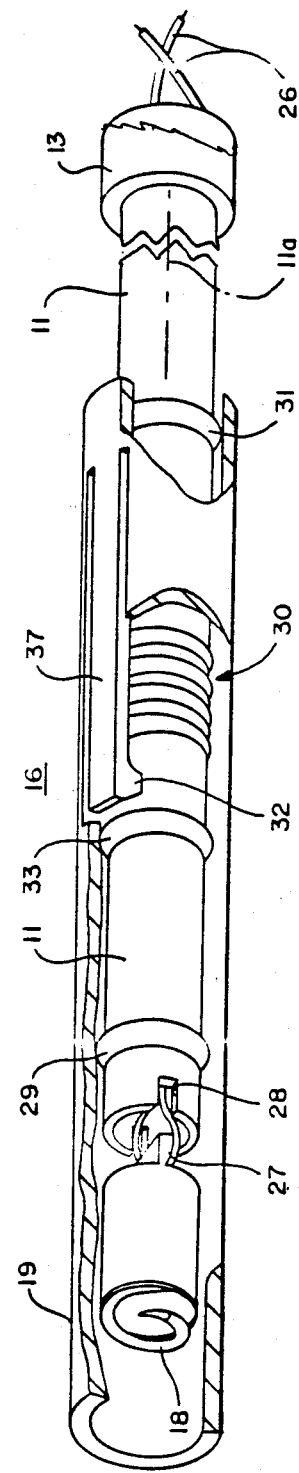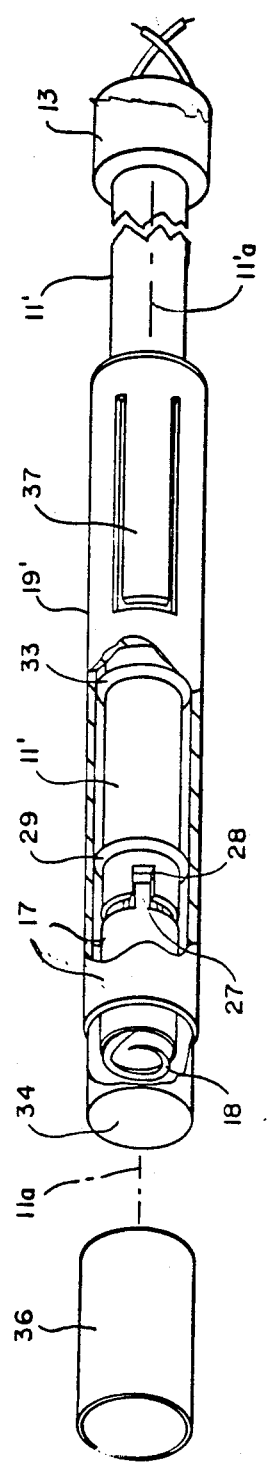

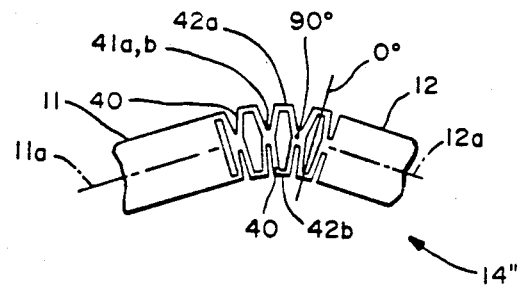
FIG.—6
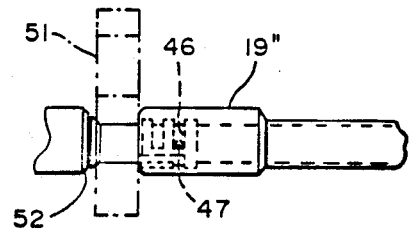
FIG.—7A
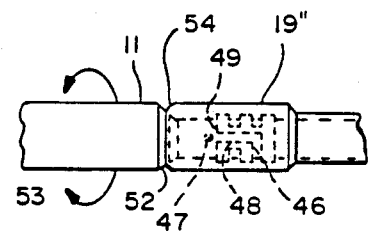
FIG.—7B
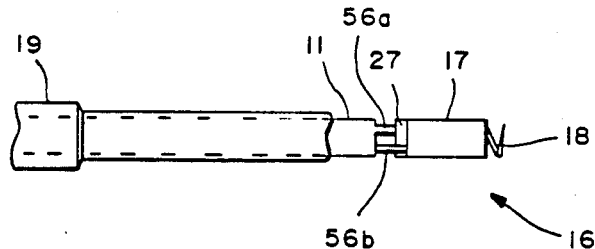
FIG.—8
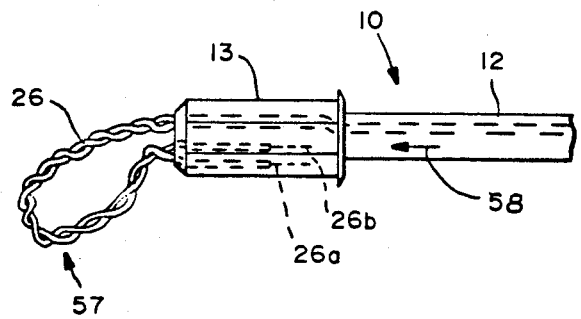
FIG.—9

ELECTRODE ASSEMBLY FOR SENSING HEART ACTIVITY

RELATED APPLICATIONS

This is a continuation of an application filed Aug. 1, 1986, Ser. No. 892,600 (now U.S. Pat. No. 4,686,996), which is a continuation-in-part of an application (now abandoned) filed Dec. 24, 1985, Ser. No. 812,967, in the name of Paul Ulbrich, entitled "Electrode Assembly for Sensing Heart Activity".

BACKGROUND OF THE INVENTION

This invention relates generally to an electrode assembly for attachment to body tissue to sense electrical heart activity. The electrode is particularly suited for insertion through the vaginal passageway of a woman in labor and for remote controlled attachment to the fetus; specifically, the head (scalp) of the fetus. The electrode provides heart signals to electronic monitoring equipment which display an EKG (electrocardiogram) signal and/or the heart rate.

In general, a remote control device for screwing a retaining coil electrode into the scalp of the fetus is shown in a number of patents, including Hon, et al., U.S. Pat. No. Re. 28,990. Here a flexible drive carries the fetal engaging electrode and is rotatably disposed within a rigid guide tube.

The proximal end of the flexible drive engages a fin on the back of the electrode holder so that when rotation is applied to the distal end of the drive (by the hand of the surgeon) rotation is transmitted to a spiral electrode which is screwed into the fetal epidermis. Thereafter, the entire drive and guide tube assembly is removed allowing the electrode to remain attached with wires going to a suitable monitoring system, and then the delivery of the child may proceed.

Other patents offer alternative methods of applying rotating force to a spiral electrode or different means therefor.

Murphy U.S. Pat. No. 4,180,080 employs a single flexible guide and a handle connected to the twisted electrode leads which are threaded through the guide tube and which are attached to the scalp engaging electrode. When the handle is rotated, this rotary motion is imparted to the spiral electrode by means of the electrode leads driving it into the fetal epidermis; here the flexible guide tube remains stationary. Since the guide tube of Murphy is flexible, it is difficult to obtain the forward force necessary to penetrate the fetal epidermis. It is also difficult to obtain a positive drive force due to the inherent flexibility of the twisted wires.

Another technique of an applicator employing a plunger at the distal end of a guide tube and means for converting the linear motion generated by depressing the plunger to rotary motion is shown in Hon U.S. Pat. No. 4,321,931; and Helfer, et al., U.S. Pat. Nos. 4,301,806, and 4,437,467. These have not received wide acceptance due to the complexity of the design and the high cost of manufacture. Furthermore, the user cannot be sure of proper electrode attachment when the plunger is depressed. Further, these designs either employ a rigid guide tube of fixed curvature or a flexible guide tube which lacks the rigidity necessary to apply forward force to the fetal engaging electrode.

OBJECT AND SUMMARY OF THE INVENTION

It is the general object of the invention to provide an improved electrode assembly for sensing heart activity from body tissue.

In accordance with the above object, there is provided an electrode assembly for sensing heart activity from body tissue comprising a cylindrical guide tube having a first axis and a first relatively rigid portion with a proximal end being affixed to a fetal engaging electrode. The guide tube includes a second relatively rigid portion having a second axis with a distal end having a rotatable handle for manually rotating the guide tube. The guide tube also incorporates a relatively flexible, pleated intermediate portion connecting the first and second portions which includes universal joint means. Sleeve means is located at the proximal end of the guide tube which is rotatable within the sleeve means. The sleeve means is also graspable whereby when the handle is rotated and the sleeve is grasped and the respective axes of the first and second cylindrical portions while coplanar are not coincident, the universal joint means accommodates the rotation.

BRIEF DESCRIPTION OF THE DRAWINGS

FIG. 1 is a side view of one embodiment of the invention.

FIG. 2 is a perspective view illustrating the use of the electrode assembly and attaching it to the epidermis of the fetus.

FIG. 3 is an enlarged crosssectional view of an intermediate portion of the guide tube of FIG. 1.

FIG. 4 is an enlarged perspective view partially cut away of one embodiment of the proximal end of the assembly of FIG. 1.

FIG. 5 is a perspective view partially cut away and partially shown in exploded form of another embodiment of the the proximal end of FIG. 1.

FIG. 6 is a side view of another embodiment of the invention.

FIGS. 7A and 7B are side views illustrating a portion of the invention in two different operative states.

FIG. 8 is a side view partially cut away, illustrating a proximal end of the present invention.

FIG. 9 is side view of a distal end of one embodiment of the invention.

DESCRIPTION OF THE PREFERRED EMBODIMENTS

FIG. 1 illustrates the overall assembly of the present invention which comprises a guide tube 10, having first and second relatively rigid cylindrical portions 11 and 12. Each of these has a cylindrical axis 11a and 12a, respectively, which as illustrated are coplanar but in an operative position, are not coincident. Second portion 12 of the guide tube has at the distal end a rotatable handle 13 for manually rotating the guide tube. The two relatively rigid portions 11 and 12 are joined by a pleated intermediate portion which, in FIG. 1, is in the form of a deformable bellows 14 to complete the total guide tube 10. The bellows, in effect, forms a universal joint to accommodate rotation of the guide tube when the axes 11a and 12a (in their position as illustrated) are not coincident.

At the proximal end 16, is mounted a rotatable electrode holder 17 which carries a spiral electrode 18, which is suitable for making electrical contact with the fetal epidermis. A sleeve 19 mounted on proximal end 16 rotates on guide portion 11 and its axis 11a. Sleeve 19 is also slidable in an axial direction to effectively protect or expose the spiral electrode 18. In addition, it has the function of a fixed bearing graspable by the fingers of the surgeon, while the handle 13 is being rotated.

The use of the electrode assembly is illustrated in FIG. 2, with a fetus 21. The fetus is shown in the mother's womb during an intermediate stage in the delivery process where the electrode assembly is introduced through the vagina or birth canal 22. The surgeon's hand 23 is grasping with two fingers sleeve 19, to both introduce the assembly into the birth canal and support sleeve 19 in its action as a fixed bearing, while the surgeon's other hand 24, rotates the handle 13 to guide the spiral electrode 18 into the fetal epidermis 25.

Electrode 18 is connected by a pair of wires 26 (see FIG. 1) to associated monitoring apparatus, to monitor the EKG or fetal heart rate of the fetus 21 in a well known manner.

Guide tube 10 is hollow to allow the pair of electrical leads 26 to pass through its center. One lead is attached directly to spiral 18, and the other to a second electrode at the opposite end of electrode holder 17. After attachment of the spiral electrode the guide tube and sleeve are removed, and the fetal ecg or fetal heart rate may be monitored by connecting the lead wires to a suitable monitor. The bellows 14 which serves as a universal joint is shown in enlarged cross-section in FIG. 3, in an expanded form. This, in fact, is the form in which it is manufactured of a plastic material, such as a polypropylene. One plastic wall 14a has a 60° angle to the central axis of the bellows and the adjacent wall 14b, a 30° angle. Thereafter, it is as illustrated in FIG. 1 and is attached to the first and second cylindrical portions 11 and 12 by a typical plastic attachment process to form one continuous guide tube 10. With such bellows the guide tube can be bent at any angle from zero to 90° and stay at that angle as is necessary in a particular delivery as illustrated in FIG. 2. The 30° and 60° combination allows the tube to be bent and stay in a bent position in a semi-rigid manner. In other words, a bellows of this type has a memory.

When the guide tube is bent, the bellows is sufficiently flexible to smoothly transmit the rotary motion imparted by the handle 13, to the spiral electrode 18. The guide tube can easily be bent to conform to the anatomy of any patient. On the other hand, the bellows although flexible is rigid enough that the necessary forward force when applied to handle 13 will be transmitted to the spiral electrode 18 to facilitate engagement with the fetal epidermis 25.

FIG. 4 illustrates the details of the proximal end 16 and sleeve 19. As stated above, the sleeve accommodates rotation and at the same time is protective in preventing the spiral electrode 18 from being exposed during introduction of the assembly through the vagina. Specifically, sleeve 19 in the position as illustrated, is extended to cover the electrode 18 which, of course, is mounted on holder 17. Electrode holder 17 carries a fin 27 which is normally engaged in a slot 28 at the end of drive portion 11 to first ensure rotation of spiral electrode 18 when engaging the fetal epidermis and secondly to allow the guide tube to be withdrawn after engagement leaving only the electrode holder 17 and leads 26 in place, for the purpose of monitoring.

To facilitate the rotation of sleeve 19 after it is retracted to expose electrode 18, around the axis 11a, there is a forward guide ring 29 and an aft guide ring 31.

To hinder movement of the sleeve means in the axial direction during insertion, the embodiment of FIG. 4 includes a set of detent rings 30 in which a pawl rides. Pawl 37 is a cut-out section of sleeve 19 with an enlarged tip 32 suitable for riding in the grooves created by the detents 30. Thus, in operation the surgeon introduces the assembly into the birth canal 22 (FIG. 2) until the end of sleeve 19 is pressing against the fetal epidermis 25; the sleeve thereupon retracts because of the continued axial force on the drive handle 13. When the last detent ring of the group 30 passes pawl tip 32, the surgeon senses the freeness of movement and rotates the drive handle to engage electrode 18 in the epidermis 25.

The last remaining ring 33 is for the purpose of stopping the forward axial movement of the sleeve 19 on tube portion 11, so that it does not accidently fall off.

FIG. 5 illustrates an alternative embodiment of the sleeve, 19' where the resisting means instead of the ring type detent 30 is a thin breakable membrane 34, which is placed or stretched over the end of sleeve 19' and then held in place by a retainer cap 36 which is slid over it. The thin membrane is made of flexible polyethylene of other similar material. It is placed perpendicular to the axis 11a. The cap 36 is approximately ½ inch in length and thus forms a recess which prevents contamination of membrane 34 by vaginal fluids and allows the membrane to rupture but not contact the fetal epidermis.

In operation when sleeve 19' is placed over the drive 11' and the spiral electrode 18, it will slide aft until the spiral electrode contacts membrane 34. The membrane thus acts as a means to resist sliding motion when the guide tube is being introduced. As stated above, it also serves as a barrier to contamination of the spiral electrode. When the sleeve 19' makes contact with the fetal epidermis as in the case of the embodiment of FIG. 4, the rotation of drive tube 10 by handle 13 causes the spiral tip to break or rupture the membrane allowing the electrode to move forward and make contact with the fetal epidermis 25. Continued rotation drives the spiral electrode 18 into the epidermis. Thus, again as in the case of the embodiment of FIG. 4, the surgeon operating the electrode assembly senses the rupturing or breaking of membrane 34 and realizes that the spiral electrode 18 is thus making initial contact with the fetal epidermis and can be rotated to make permanent contact.

FIG. 6 illustrates an alternative embodiment of the universal joint 14" which connects the two cylindrical portions 11 and 12. Universal joint 14" consists of a number of rings 40 which are two sided and which are flexibly connected to one another by a pair of pivot points located at the ends of two orthogonal diameters through each ring and with one diameter being displaced 90° from the other. The entire joint is constructed of any convenient flexible plastic material. One pair of pivot points 42a and 42b, essentially lie along an axis designated 0° and the pair on the other side of the ring designated 41a, 41b, lie along an axis designated 90°, only the end of which is visible, of course. These axes are, of course, orthogonal or 90° from each other. With this type of connection and with the use of multiple rings, flexibility is easily achieved through 360° of rotation at even a 90° angle between the axes of 11a, 12a and portions 11 and 12.

FIGS. 7A and 7B illustrate a resistance technique for a modified sleeve 19". As illustrated in FIG. 7A and 7B, there is a circumferential groove 46 in which a round protrusion 47 extending from the interior of sleeve 19", rides or is slidable. In other words, this is an interior guide for the sleeve which is guided by the circumferential groove 46. This groove is best illustrated in FIG. 7B and then connects at a right angle to a longitudinal groove 48 which, of course, has one end connected to the circumferential groove 46 and is open at its other end 49. When the interior guide 47 is at this other end as shown in FIG. 7B, it is obvious that the sleeve 19" is freely rotatable on the rigid portion 11. Thus, in operation initially when the electrode assembly of the present invention is supplied, the sleeve 19" is locked into the position shown in FIG. 7A by a safety clip 51, constructed, for example, of flexible plastic. This abuts against the end of sleeve 19" and the chamfered end 52 of the rigid portion 11. This assures that the sleeve 19" is maintained in its locked position with its interior guide 47 against the end of the groove 46; that is the end of the groove opposite its connection with longitudinal groove 48. Thus there can be no retractable movement of the sleeve 19" to expose the tip of the electrode. Thereafter, once in the user's hands, the clip 51 is removed and the assembly used in the normal manner until the end of the sleeve 19" abuts against, for example, the infant's head. At this point, the surgeon rotates by the use of the manual nob 13, the drive tube 102° in the direction as indicated by the arrow 53 until the guide 47 abuts against the longitudinal groove 48 and then the sleeve may be retracted along the longitudinal groove until the chamfered end of the sleeve 54 abuts against the chamfered end 52 of portion 11. This chamfering or beveling prevents the pinching of any tissue.

In order to prevent excessive torque being applied to the assembly and to the electrode tip 18 while it is being screwed into the fetal epidermis, there is provided safety release means as illustrated in FIG. 8. Here the end of sleeve 19 and tube portion 11 is shown with the electrode 18 and the electrode holder 17, having a fin 27. In accordance with the invention, the fin 27 is retained by a pair of flexible fingers 56a and 56b which are opposite each other at the end 16 of the tube portion 11, and which engage opposite sides of the fin-like member 27. When a predetermined torque is applied to the rotatable handle 13 (see FIG. 1), then these will bend sufficiently to allow free rotational movement between the proximal end 16 and the electrode 18. The length of the flexible fingers 56a and 56b determines the amount of torque. Typically they are constructed of the same material as the tube portion 11. This release method prevents damage to the fetal skin due to over driving.

In order to axially retain the electrode assembly 17 with its fin 27 as illustrated in FIG. 8, against the fingers 56a, 56b, as illustrated in FIG. 9, the pair of wires 26 extending from out of the handle 13 of the tube portion 12, are looped as illustrated at 57, back into the handle 13. Thus, the wire ends 26a and 26b are shown contained within the handle portion 13 to provide a restraining force in the direction of arrow 58 so that the electrode assembly 17, 18, does not actually pull away from the proximal tube end 16. In operation, after the electrode 18 has engaged the fetal epidermis, the loop 57 is pulled out of handle 13 and the entire drive tube 10 is removed leaving only the leads attached to the electrode assembly 17, 18. Then, of course, the leads, as discussed above, are attached to monitoring equipment. Thus, besides providing a retaining force for the electrode assembly 17, 18, retaining the end of the leads 26a, 26b, within handle 13, also protects the bare ends from contamination and also prevents them from damaging surrounding tissue.

Thus, in summary, an improved electrode assembly for sensing heart activity in body tissue has been provided.

What is claimed:

1. A fetal electrode product comprising:
   an electrode assembly having a spiral electrode extending from its forward end;
   a guide tube having a forward end and including means for releasably engaging said electrode assembly for rotating said spiral electrode, said guide tube having at least a flexible, pleated, intermediate section so that the guide tube can conform to the contour of the birth canal of a woman in labor, said flexible, pleated, intermediate section functioning as a universal joint so that said guide tube can be rotated within the birth canal to attach the spiral electrode to the fetus;
   a protective sleeve covering said spiral electrode and the forward end of said guide tube, the length of the sleeve relative to said guide tube being short enough that the sleeve does not affect the ability of the guide tube to conform to the curve of the birth canal.

2. A fetal electrode product according to claim 1, wherein the forward end of the guide tube includes guide rings on its outer surface engaging the inner surface of said protective sleeve.

3. A fetal electrode product according to claim 2, including resistance means for hindering the movement of said sleeve relative to said guide tube, said resistance means providing an indication of when the sleeve has been moved to a position in which the spiral electrode is no longer protected by the sleeve.

4. A fetal electrode product according to claim 3, wherein said resistance means includes a breakable membrane stretched across the end of said sleeve closest to said spiral electrode.

5. A fetal electrode product according to claim 3, wherein said resistance means includes a plurality of annular detents on said guide tube and pawl means on said sleeve for interacting with said detents.

6. A fetal electrode product according to claim 3, wherein said resistance means includes a circumferential groove around at least part of the periphery of said guide tube and a longitudinal groove on said guide tube connected at one end to said circumferential groove and open at the other end, said sleeve including an interior projection slidable in said grooves from a first locked position in said circumferential groove to a freely rotatable position at said opened end of said longitudinal groove.

7. A fetal electrode product according to claim 6, including a safety release means comprising a fin-like member extending from said electrode assembly and a pair of flexible fingers extending from the forward end of said guide tube and engaging opposite sides of said fin-like member.

8. An electrode assembly according to claim 1, wherein said flexible, pleated, intermediate section comprises a deformable bellows.

9. An electrode product according to claim 1, wherein said flexible, pleated, intermediate section comprises a plurality of two sided rings flexibly connected to one another by a pair of pivot points located at the ends of two orthogonal diameters through each said ring with a pair of pivot points for one side of each ring being displaced 90° from said pair of pivot points for the other side of each ring.

* * * * *